US009597500B2

(12) United States Patent
Chib et al.

(10) Patent No.: US 9,597,500 B2
(45) Date of Patent: Mar. 21, 2017

(54) REMOTE ACTIVATION OF THE MIDBRAIN BY TRANSCRANIAL DIRECT CURRENT STIMULATION OF PREFRONTAL CORTEX

(71) Applicant: California Institute of Technology, Pasadena, CA (US)

(72) Inventors: Vikram Chib, Baltimore, MD (US); Kyongsik Yun, Seoul (KR); Hidehiko Takahashi, Kyoto (JP); Shinsuke Shimojo, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 14/316,306

(22) Filed: Jun. 26, 2014

(65) Prior Publication Data

US 2015/0005568 A1     Jan. 1, 2015

Related U.S. Application Data

(60) Provisional application No. 61/839,779, filed on Jun. 26, 2013.

(51) Int. Cl.
*A61N 1/36*       (2006.01)
*A61N 1/04*       (2006.01)
*A61N 2/00*       (2006.01)

(52) U.S. Cl.
CPC ....... *A61N 1/36025* (2013.01); *A61N 1/0492* (2013.01); *A61N 2/006* (2013.01)

(58) Field of Classification Search
CPC .... A61N 1/36; A61N 1/36025; A61N 1/3605; A61N 1/36082; A61N 1/05; A61N 1/0551; A61N 2/00; A61N 2/004
USPC ............................... 600/9; 607/45, 115–117
See application file for complete search history.

(56) References Cited

U.S. PATENT DOCUMENTS

| | | | |
|---|---|---|---|
| 2004/0111127 A1* | 6/2004 | Gliner | A61N 1/36167 607/45 |
| 2006/0004422 A1* | 1/2006 | De Ridder | A61N 1/0529 607/45 |
| 2007/0027500 A1* | 2/2007 | Maschino | A61N 1/36082 607/45 |
| 2011/0288610 A1* | 11/2011 | Brocke | A61M 21/02 607/45 |

\* cited by examiner

*Primary Examiner* — Christopher D Koharski
*Assistant Examiner* — Roland Dinga
(74) *Attorney, Agent, or Firm* — Seth D. Levy; Nixon Peabody LLP

(57) ABSTRACT

A method and system of remotely stimulating the midbrain area is disclosed. Transcranial direct current stimulation is applied via a cathode attached to the right dorsolateral prefrontal cortex and an anode attached to the ventromedial prefrontal cortex. These regions are either directly connected or indirectly connected to the midbrain region. The stimulation allows non-invasive stimulation of neurons in the midbrain region to address brain disorders such as Parkinson's disease, schizophrenia, depression and addiction.

10 Claims, 10 Drawing Sheets

FIG. 4E

| Region | Laterality | x | y | z | z-score |
|---|---|---|---|---|---|
| Motor Cortex | L | -33 | -33 | 57 | 7.70 |
| Cerebellum | R | 21 | -51 | -24 | 4.91 |
| Primary Auditory Cortex | L | -54 | -15 | 6 | 3.50 |
| Ventromedial Prefrontal Cortex | L | -9 | 39 | -6 | 3.42* |
| Anterior Cingulate | C | 0 | 39 | 6 | 3.36 |

FIG. 4F

| Region | Laterality | x | y | z | z-score |
|---|---|---|---|---|---|
| Ventral Midbrain | C | 0 | -15 | -15 | 3.64* |

FIG. 5E

| Region | Laterality | x | y | z | z-score |
|---|---|---|---|---|---|
| Ventral Midbrain | L | -12 | -15 | -21 | 4.23* |
| Frontal Eye Fields | R | 30 | 48 | 42 | 3.54 |
| Frontal Eye Fields | L | -15 | 51 | 45 | 3.46 |
| Orbitofronal Cortex | L | -21 | 30 | -15 | 3.33 |

REMOTE ACTIVATION OF THE MIDBRAIN BY TRANSCRANIAL DIRECT CURRENT STIMULATION OF PREFRONTAL CORTEX

COPYRIGHT

A portion of the disclosure of this patent document contains material that is subject to copyright protection. The copyright owner has no objection to the facsimile reproduction by anyone of the patent disclosure, as it appears in the Patent and Trademark Office patent files or records, but otherwise reserves all copyright rights whatsoever.

PRIORITY

The present application claims priority to U.S. Provisional Application 61/839,779 filed on Jun. 26, 2013, which is hereby incorporated by reference in its entirety.

TECHNICAL FIELD

The present disclosure relates generally to treating brain disorders and specifically electrically stimulating frontal regions in a brain to remotely stimulate midbrain areas.

BACKGROUND

The midbrain lies deep within the brain and has an important role in reward motivation, movement, and pathophysiology. Dopaminergic neurons (i.e., neurons whose primary neurotransmitter is dopamine) are comparatively few in number in the human brain and their cell bodies are confined to a few relatively small brain areas such as the substantia nigra and ventral tegmental areas of the midbrain. Dopaminergic neurons in the substantia nigra and ventral tegmental areas project to numerous areas in the brain and exert powerful effects on their targets. Impairments in the dopaminergic function of these areas of the midbrain have been implicated in various neuropsychiatric disorders such as Parkinson's disease, schizophrenia, depression, and addiction. These conditions may be addressed by stimulation of the midbrain resulting in dopamine increases to stimulate neurons.

Given that substantia nigra and ventral tegmental area neurons lie deep within the brain, the primary means of influencing the midbrain has been either systematic pharmacological interventions or implantation of deep brain stimulators. Systematic pharmacological intervention is the first line of therapy for many neurological and neuropsychiatric disorders. Currently, treatment for such conditions involves pharmacological intervention to increase dopamine levels. Unfortunately, a pharmaceutical's effect is difficult to localize and therefore increases dopamine to all areas of the brain including non-affected sections, precluding region-specific interventions. Further, some patients with these disorders do not respond to the drug therapy.

For subjects that do not respond to pharmacological intervention, invasive deep brain stimulation may be considered. However, since the midbrain is deep within the brain, such stimulation techniques require invasive procedures to insert the stimulator, thus disrupting normal functions and increasing risk to the subject.

The two predominant means of non-invasively stimulating the brain are transcranial magnetic stimulation (TMS) and transcranial direct current stimulation (tDCS). Transcranial magnetic stimulation involves inducing an electrical current within the brain via a pulsating magnetic field applied by an induction coil stimulator placed above the scalp. Transcranial direct current stimulation involves the application of a small current between anodal and cathodal electrodes placed on the scalp. Both of these stimulation methods result in changes in brain function by causing neurons' resting membrane potential to depolarize or hyperpolarize.

There is therefore a need for a method of brain repair that non-invasively stimulates neurons in midbrain regions. There is a further need for a system that allows stimulation of the prefrontal cortex in order to utilize indirect and direct connections to activate and deactivate the midbrain area.

SUMMARY

According to one example, a method of stimulating the midbrain interconnected with the prefrontal cortex of the brain is disclosed. An electrical stimulator is attached near the prefrontal cortex of the brain. The prefrontal cortex is stimulated via the electrical stimulator to remotely activate the midbrain of the brain.

Another example is a system for compensating for disorders in the midbrain. The system includes a controller and a stimulator for stimulation of the selected frontal node of the brain circuit. The stimulator is operable to provide stimulation to the midbrain via pulses controlled by the controller. The pulses are applied to the prefrontal cortex through direct or indirect connections to the midbrain.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 4E is a table of conjunction analysis between regions showing a signal positively correlated with attractiveness ratings before and after stimulation in the main stimulation and the active sham groups;

FIG. 4F is a table of regions showing an interaction between attractiveness ratings before and after stimulation in the main group as compared to the active sham group;

FIG. 5E is a table including regions showing increased stimulation related functional connectivity with the ventromedial prefrontal cortex in the main stimulation group compared to the active sham group.

Figure 1:
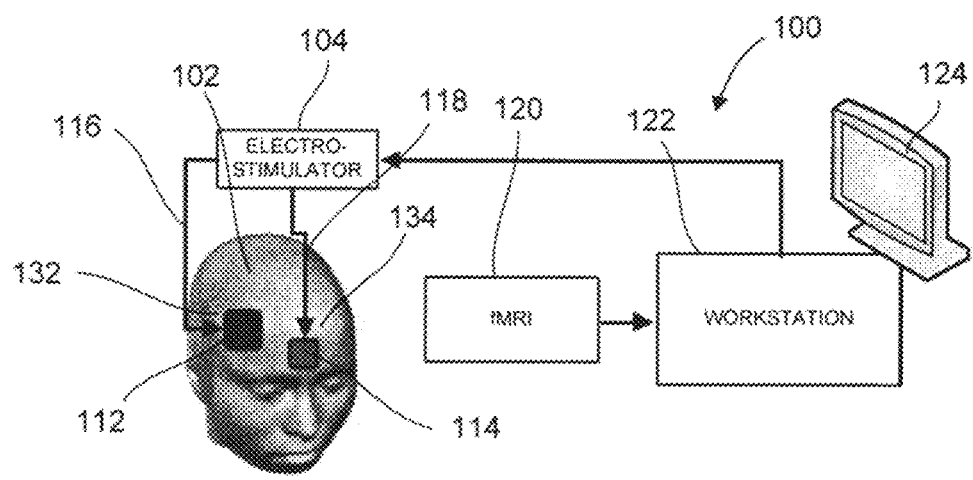
FIG. 1 is a block diagram of a brain stimulation system to non-invasively stimulate a midbrain region of a subject.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

FIG. 1 shows a midbrain stimulation system 100 that is directed to treatment of a patient by stimulating the midbrain areas of a subject 102 having a disorder effecting midbrain functions. The system 100 includes a stimulator such as an electrical stimulator system 104 that includes a cathode electrode 112 and an anode electrode 114 that are attached to the head of the subject 102. As will be explained below, the electrical stimulator system 104 generates current between the cathode electrode 112 and the anode electrode 114 through respective wires 116 and 118. Alternatively, the stimulator may be implanted just under the surface of the skin of the subject 102 over the areas explained below.

The system 100 includes an optional imaging device 120 that is coupled to a workstation 122 having a display 124. In this example, the imaging device 120 is a functional magnetic resonance imager (fMRI). However, other imaging or recording devices such as an electroencephalogram (EEG) system, or other real time brain imaging system may be used. The imaging device 120 is used to scan the brain of the subject 102 to monitor the stimulation of the prefrontal cortex and/or the midbrain. The workstation 122 allows control of the stimulator system 104 and the imaging device 120 for duration and intensity of the stimulation to the subject 102. In this example, the workstation 122 is a controller that controls electrical pulses applied by the stimulator system 104. Imaging of the brain can take place either in real-time, during brain stimulation, or before or after stimulation. It is also possible that closed loop stimulation may be employed in which the stimulation procedure is modified and updated based on brain image recordings of the stimulation. In such a closed loop stimulation, the workstation 122 may include software to analyze the brain image recordings and modify the electrical stimulation applied by the stimulator system 104 accordingly. Recordings of brain activity may be streamed into the workstation 122 for control of the brain stimulator system 104. Stimulation would be contingent on the level of brain activity meeting some specified criterion, such as exceeding some predefined level of brain activation. In this way stimulation levels will be adapted depending on the amount of brain activity recorded.

In this example, the stimulator system 104 is a transcranial direct current stimulation system such as a DC-Stimulator available from neuroConn GmbH of Germany. Of course other transcranial direct current stimulation devices may be used. The anode electrode 114 provides positive stimulation while the cathode electrode 112 provides negative stimulation. Positive stimulation (as in the cases of transcranial magnetic stimulation and anodal transcranial direct current stimulation) causes a depolarization of the resting membrane potential, leading to increases in neuronal excitability and more spontaneous cell firing. Negative stimulation (in the cases of cathodal transcranial direct current stimulation) causes hyperpolarization of the resting membrane potential, leading to decreases in neuronal excitability and decreased spontaneous cell firing. Transcranial direct current stimulation is generally applied in order to induce cortical changes that persist after stimulation, while transcranial magnetic stimulation may be used to induce online cortical changes as well as changes that persist after stimulation. In both the cases, the duration and effects of stimulation increase as the duration of stimulation increases and the strength of the current increases.

The benefits of transcranial direct current stimulation over transcranial magnetic stimulation, from a logistic therapeutic perspective, are that transcranial direct current stimulation units are relatively more inexpensive and mobile in comparison to transcranial magnetic stimulators. Both transcranial magnetic stimulation and transcranial direct current stimulation are only capable of stimulating the cortical surface, which may be used by the system 100 to exploit the interconnected neural network to induce remote changes in deep brain activity such as activity in the midbrain. Other types of stimulators such as ultrasound stimulators could be used.

The head of the subject 102 shows the placement of the cathode electrode 112 and the anode electrode 114. The cathode electrode 112 is attached over a right lobe area 132 while the anode electrode 114 is attached over a forehead area 134. In this example, the cathode and anode electrodes 112 and 114 are conductive-rubber electrodes, preferably placed over two saline-soaked sponges on the areas 132 and 134. In this example, the cathode electrode 112 has a larger contact area than the contact area of the anode electrode 114 to allow for more focal stimulation of the frontal cortex. As explained above, the anode electrode 114 provides positive stimulation of the ventromedial prefrontal cortex, which lies under the forehead area 134 while the cathode electrode 112 provides negative stimulation of the right dorsolateral prefrontal cortex, which lies under the right lobe area 132. As will be explained below, the stimulation of the right dorsolateral prefrontal cortex allows stimulation of the midbrain region through either direct or indirect connection thereby remedying deficiencies in the midbrain region.

The effectiveness of anodal transcranial direct current stimulation of frontal cortex in rodents results in significantly increased neural activity in the frontal cortex and interconnected midbrain regions following stimulation. This also results in an increase in intracellular dopamine in these distal regions. The increases in activity and intracellular dopamine in the midbrain are caused by the direct transcranial direct current stimulation of the frontal cortex allowing exploitation of the highly interconnected nature of cortical brain regions to stimulate deep brain dopaminergic areas that are not directly accessible with noninvasive stimulation methods. The results from experiments with rodents show increased midbrain dopaminergic functions, in response to anodal transcranial direct current stimulation of frontal cortex.

Figure 2A:
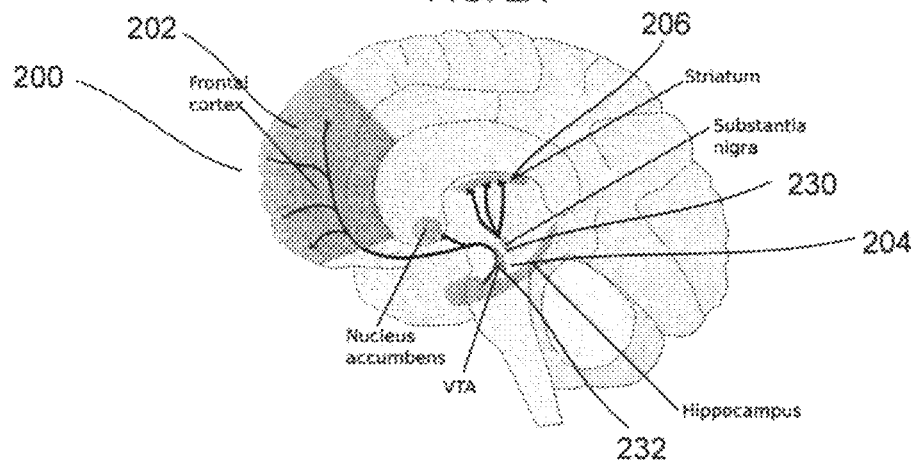
FIG. 2A is a block diagram of a model of the nodes of the brain connected to the midbrain region.
Figure 2B:
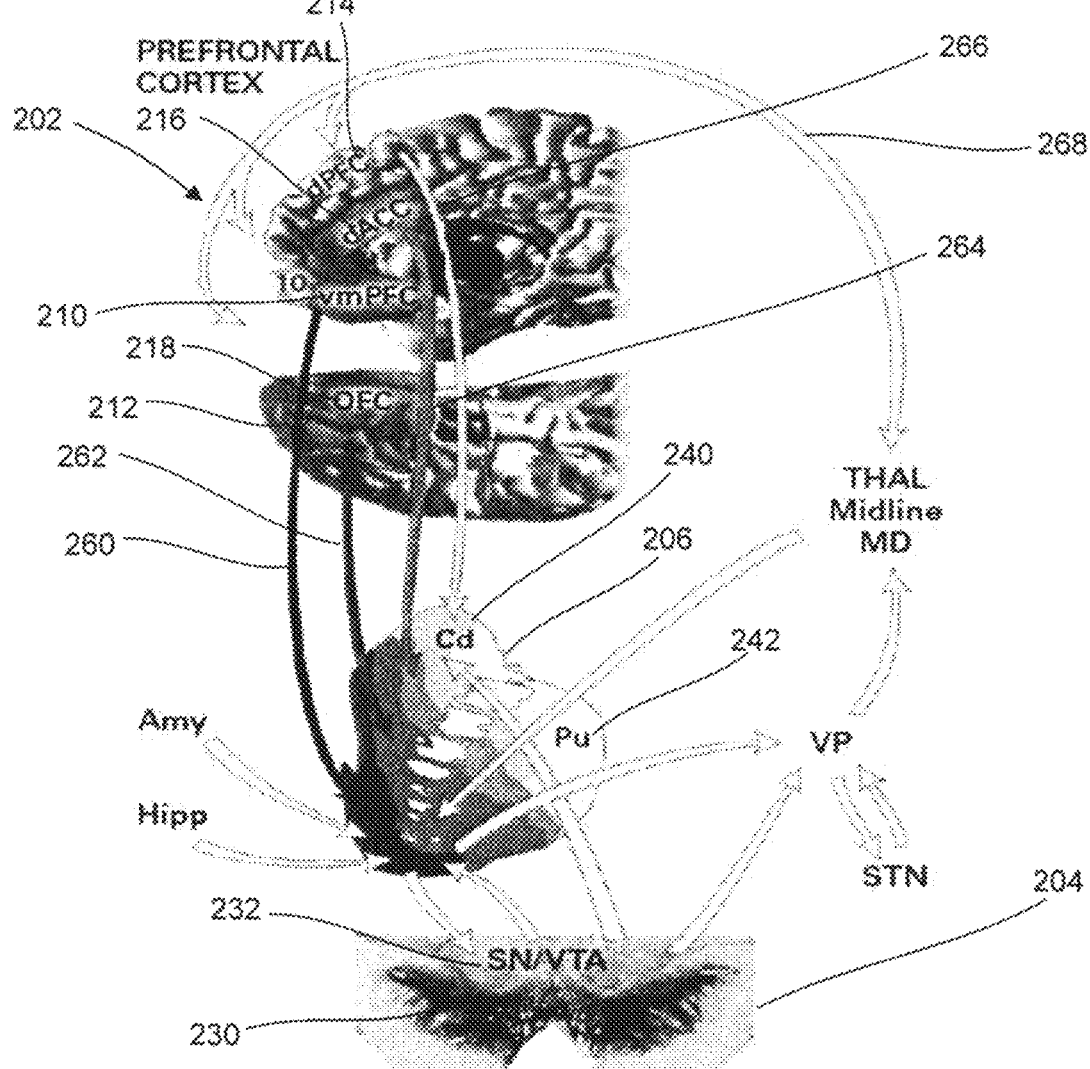
FIG. 2B is an exploded view diagram of the relevant areas of the brain for indirect stimulation via direct and indirect connections.

FIG. 2A is a diagram of a brain 200 of a subject similar to the subject 102 in FIG. 1 and FIG. 2B is an exploded diagram of the interconnections between various regions of the brain 200. The brain 200 includes a frontal cortex region 202, a midbrain area 204 and a striatum 206.

The frontal cortex region 202 includes a ventromedial prefrontal cortex (VMPFC) area 210, a left dorsolateral prefrontal cortex (DLPFC) area 212, a right dorsolateral prefrontal cortex 214, a dorsal anterior cingulate cortex (dACC) 216, and an orbital frontal cortex (OFC) 218. The left prefrontal cortex 212 preferentially processes categorical spatial memory including source memory (reference to spatial relationships between a place or event), while the right prefrontal cortex 214 preferentially processes coordinate spatial memory including item memory (reference to spatial relationships between features of an item). The ventromedial prefrontal cortex 210 also includes Fp1, Fp2, and glabella areas (not shown).

Figure 2C:
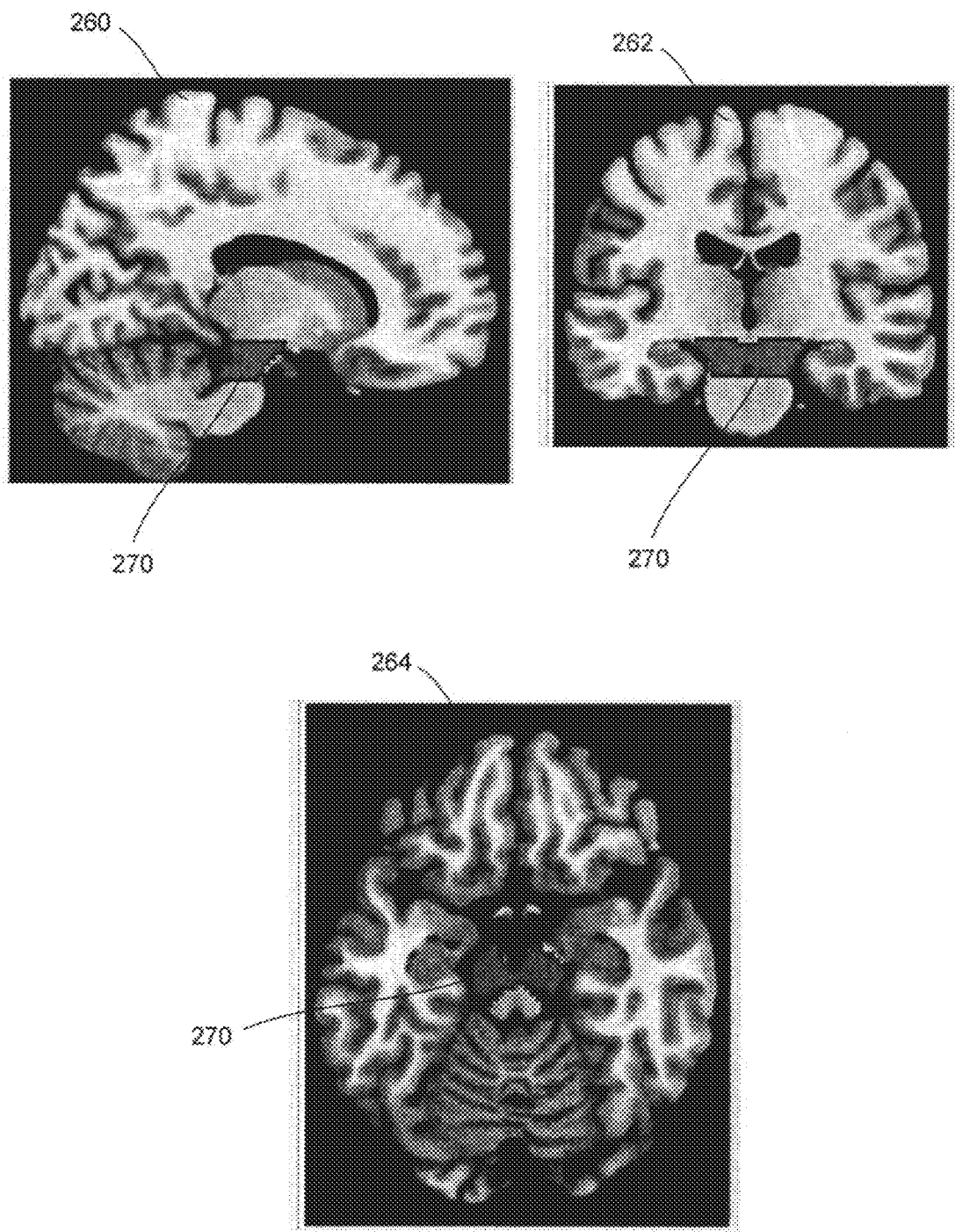
FIG. 2C are fMRI scans of the region of interest in the midbrain for non-invasive stimulation.

The midbrain area 204 includes a substantia nigra (SN) area 230 and a ventral tegmental area (VTA) 232, which both have neurons that are stimulated by dopamine. FIG. 2C shows a series of fMRI scans including a side view fMRI scan 260, a bottom view fMRI scan 262, and a top view fMRI scan 264. The scans 260, 262, and 264 each show a region of interest 270 of the ventral midbrain area 204, which was the subject of the tests described below. The region of interest 270 includes the substantia nigra 230 and the ventral tegmental area 232.

The striatum 206 helps coordinate motivation with body movement. It facilitates and balances motivation with both higher-level and lower-level functions, such as inhibiting one's behavior in a complex social interaction and fine-motor functions of inhibiting small voluntary movement. The striatum 206 includes a caudate nucleus (Cd) area 240 and a putamen area (Pu) 242.

FIG. 2B is an exploded diagram showing key structures and pathways of the reward circuit of the brain 200. A black arrow 260 represents the input from the ventromedial prefrontal cortex area 210. An arrow 262 represents the input from the orbital frontal cortex 218. An arrow 264 represents the input from the dorsal anterior cingulate cortex 216. An arrow 266 represents the input from the left dorsolateral prefrontal cortex area 212 and the right dorsolateral prefrontal cortex 214. The network of arrows 268 represents other main connections of the reward circuit, which include connections to the amygdala (Amy), the hippocampus (Hipp), the medial dorsal nucleus of the thalamus (MD), the subthalamic (STN), the thalamus (Thal), and the ventral pallidum (VP) as shown in FIG. 2B.

Given the frontal cortex 202 is close to the cortical surface as well as its direct and indirect efferent projections (via the striatum 206) and functional synchrony with the ventral midbrain 204, the ventromedial prefrontal cortex 210 and right dorsolateral prefrontal cortex 214 serve as excellent locations for direct stimulation in order to induce remote deep brain activity in humans. A number of studies have associated increases in ventromedial prefrontal cortex activity and decreases in dorsolateral prefrontal cortex activity with increases in midbrain activity and intracellular dopamine. Furthermore, the dorsolateral prefrontal cortex has been implicated in monitoring goal-directed behaviors and valuations that are encoded by the ventromedial prefrontal cortex 210. With these relationships, excitatory/anodal and inhibitory/cathodal transcranial direct current stimulation electrode placement over the ventromedial prefrontal cortex 210 and right dorsolateral prefrontal cortex 214, respectively as shown in FIG. 1, result in the remote activation of the ventral midbrain 204 in FIG. 2A. Cathodal stimulation of the dorsolateral prefrontal cortex 214 suppresses its control over the ventromedial prefrontal cortex 210, which boosts the anodal stimulation of the dorsolateral prefrontal cortex 214, and this enhanced ventromedial prefrontal cortex stimulation yields an increased remote activation of the distally interconnected ventral midbrain 204. Remote activation manifests behaviorally as increases in a subject's rewarding appraisals as may be determined by images from the imaging device 120 in FIG. 1.

Confirmation of the non-invasive stimulation technique via transcranial direct current stimulation was made based on testing for a behavioral task of rewarding appraisals. This behavioral task was selected because discrimination of facial attractiveness and emotions are commonly disrupted in neuropsychiatric disorders such as depression, schizophrenia, and Parkinson's disease. Ninety-nine right-handed healthy participants took part in this experiment (mean age, 22.9±3.95 years; range 18-37 years), of which 47 were female. The participants had no history of neurological or psychiatric illness.

Figure 3A:
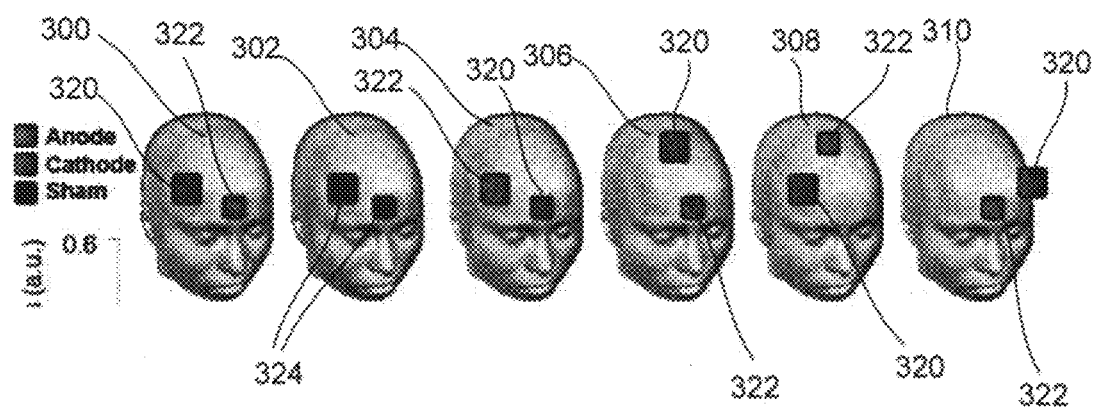
FIG. 3A is a diagram of the placement of electrodes on the various subject groups in testing.

FIG. 3A is a diagram of the placement of the anode and cathode electrodes on different subjects divided into different groups. FIG. 3A shows a subject 300 of a main group, a subject 302 of a sham group, a subject 304 of an active sham group, a subject 306 of a first control group, a subject 308 of a second control group, and a subject 310 of a third control group. As shown in FIG. 3A, a cathode 320 was placed above the right dorsolateral prefrontal cortex and an anode 322 was placed above the ventromedial prefrontal cortex in the subject 300 of the main group (19 subjects, 6 females). Sham electrodes 324 (no current applied) were placed above the right dorsolateral prefrontal cortex and the ventromedial prefrontal cortex in the subject 302 of the sham group (20 subjects, 8 females). The anode 322 was placed above the right dorsolateral prefrontal cortex and the cathode 320 was placed near the ventromedial prefrontal cortex in the subject 304 of the active sham group (16 subjects, 6 females). The cathode 320 was placed above the vertex with the center of the Cz area and the anode 322 was placed above the ventromedial prefrontal cortex in the subject 306 of the first control group (15 subjects, 7 females). The cathode 320 was placed above the right dorsolateral prefrontal cortex and the anode 322 was placed above the vertex in the subject 308 of the second control group (15 subjects, 10 females). The cathode 320 was placed above the left dorsolateral prefrontal cortex and the anode 322 was placed above ventromedial prefrontal cortex in the subject 310 of the second control group (14 subjects, 10 females).

Participants made attractiveness ratings of a series of 140 faces generated with computer software (FaceGen available from Singular Inversions of Toronto, ON, Canada). 70 male and 70 female Caucasian/European neutrally expressive faces were randomly constructed. The attractiveness of these faces was rated on an eight-point scale ranging from 0 to 7. Before the experiment, a separate group of 20 observers rated these faces. Based on these ratings, the series of 140 faces were divided into two sets. Using the preliminary ratings, these two groups of faces were uniformly distributed across the range of attractiveness and had the same means and standard deviations of attractiveness ratings (before-stimulation set: 3.66±1.00; after-stimulation set: 3.66±1.02).

These attractiveness-balanced sets of faces allowed control for possible mere exposure effects that could occur if the same set of faces were used before and after stimulation.

The experiment was divided into three sessions. During the first session (before stimulation), participants made facial attractiveness judgments. During the second session, participants were treated with transcranial direct current stimulation for 15 minutes. Finally, during the final session (after stimulation), participants again made facial attractiveness judgments. To assess the behavioral effects of transcranial direct current stimulation, participants were asked to make attractiveness ratings of faces. As described above, two sets of attractiveness-balanced faces were used. One served as a before-stimulation test set, the other an after stimulation test set. The faces in each set were presented in randomized order. In every trial, participants were presented with a face to rate the attractiveness on an eight-point scale. Participants made a rating by selecting one of the eight buttons on two button-press response pads. One response pad was placed in each hand of the participant, and ratings progressed from the left hand fourth phalange being 0 to the right hand fourth phalange being 7. Participants had 4 seconds to make a rating, after which their rating value was presented to them for 1 second, followed by a pseudo-randomly (~1-10 s) jittered blank screen. Trials in which subjects did not make a selection in the allotted time were assigned as "missed responses."

To assess the neural effects of transcranial direct current stimulation, the two groups of participants were scanned with functional magnetic resonance imaging (fMRI) while making facial attractiveness ratings. These participants were removed from the scanner during administration of transcranial direct current stimulation. Functional imaging was conducted using a 3.0 Tesla Trio MRI scanner to acquire gradient echo T2*-weighted echoplanar (EPI) images with blood oxygenation-level-dependent (BOLD) contrast. To optimize functional sensitivity in the frontal cortex, a key region of interest (ROI), the images were acquired in an oblique orientation of 30° to the anterior commissure-posterior commissure line. In addition, a 12-channel-phased array coil was used to boost the MRI signal. Each volume of images had 44 axial slices. The imaging parameters were as follows: echo time of 30 ms; field of view of 192 mm$^2$; in-plane resolution and slice thickness of 3 mm (no gap); and repetition time of 2.75 seconds. Whole-brain high-resolution T1-weighted structural scans (1×1×1 mm$^3$) were acquired for each participant, co-registered with their mean EPI images and averaged across participants to permit anatomical localization of the functional activations at the group level.

The transcranial direct current stimulation was delivered using a battery driven constant-current stimulator (DC-Stimulator available from neuro-Conn GmbH of Ilmenau, Germany), through conductive-rubber electrodes, placed over two saline-soaked sponges. Of course other types of transcranial direct current stimulation devices may be used. To allow for more focal stimulation in the main stimulation condition (anode placement over the ventromedial prefrontal cortex, cathode placement over the right dorsolateral prefrontal cortex), two sizes of electrodes were used. In the main condition, the smaller-sized anode electrode 322 had a contact area of 3.5 cm×3.5 cm (12.25 cm$^2$, current density, 0.16 mA cm$^{-2}$) and was placed over the ventromedial prefrontal cortex as shown in FIG. 2A, and the larger-sized cathode electrode 320 had a contact area of 5 cm×5 cm (25 cm$^2$, current density, 0.08 mA cm$^{-2}$) and was placed over right dorsolateral prefrontal cortex. The electrodes were placed differently in all stimulation conditions. During active stimulation conditions, transcranial direct current stimulation was performed for 15 min and at 2 mA intensity (20 second ramp in and 20 second ramp out). The impedance was controlled by the device, normally ranging <10 kΩ, limited by the voltage at <26 V. Similar stimulation parameters are commonly used to elicit behavioral responses from transcranial direct current stimulation. Stimulation sates were localized using a combination of the 10-20 international system for EEG placement and anatomical landmarks. The experiment involved four stimulation sites of interest (the ventromedial prefrontal cortex, the right dorsolateral prefrontal cortex, the left dorsolateral prefrontal cortex, and the vertex) as shown in FIG. 3A. To stimulate the ventromedial prefrontal cortex 210, the anode electrode 322 was placed with its center halfway between Fp1 and Fp2 areas and over the glabella area. To stimulate the right and left dorsolateral prefrontal cortex, the cathode electrode 320 was placed over the F4 and F3 area, respectively for the different placements. This method of dorsolateral prefrontal cortex localization has been used in transcranial direct current stimulation and transcranial magnetic stimulation studies and has been confirmed as an accurate method of localization. To stimulate the vertex, an electrode was placed over the center of the Cz area. Given the low spatial resolution and diffuse current spread of transcranial direct current stimulation, it is common to localize stimulation locations using EEG landmarks as opposed to participant specific neuroanatomy.

The control conditions were used to confirm that the effects of anodal transcranial direct current stimulation of the ventromedial prefrontal cortex and cathodal transcranial direct current stimulation of right dorsolateral prefrontal cortex in the main group were specific to this stimulation orientation and polarity. The only condition that resulted in a significant increase in attractiveness ratings was the main stimulation condition. The resulting data from each of the groups (main, sham, active sham, control 1, control 2, and control 3) is shown in a graph 350 shown in FIG. 3B. The graph 350 charts normalized attractive ratings taken from the subjects of each group before and after stimulation.

Participants in the main stimulation group and the active sham group were scanned with an fMRI during the sessions in which they made attractiveness ratings. The imaging analysis was focused on these two groups to examine the neural effects of the main condition as compared with the third control stimulation group. The third control stimulation group mirrored the main stimulation condition without resulting in a significant behavioral effect. Participants in these groups were removed from the fMRI scanner during the stimulation. This allowed examination of changes induced by the transcranial direct current stimulation in neural functions associated with significant behavioral changes (main group), as compared with a control stimulation condition that did not result in a significant behavioral effect (active sham group).

Raw attractiveness ratings were skewed toward zero. Max-normalization of the ratings was used dividing participant ratings by their maximum attractiveness rating. This normalization allowed correction for participants' use of abbreviated ranges of the rating scale. To confirm that the rating data was normal, a Kolmogorov-Smirnov test was performed (before stimulation: P=0.163; after stimulation: P=0.20). Analysis of variance was used for repeated measures to investigate whether there was a difference between before/after stimulation and the various stimulation groups. Planned comparisons were performed using paired t-tests to investigate whether there was a difference between before- and after-stimulation conditions in each group.

Image analysis was performed using SPM8 software (available from the Wellcome Department of Imaging Neuroscience, Institute of Neurology, London, UK). Images were corrected for slice acquisition time within each volume, motion corrected with realignment to the first volume, spatially normalized to the standard Montreal Neurological Institute EPI template and spatially smoothed using a Gaussian kernel with a full width at half maximum of 8 mm. Intensity normalization and high-pass temporal filtering (using a filter width of 128 s) were also applied to the data.

To analyze the data, participant-specific (first-level) general linear models were estimated using a first-order autoregressive model. This model was designed to identify regions in which BOLD activity was parametrically related to attractiveness ratings and was estimated for the experiment phases in which participants made attractiveness ratings. The general linear model included the following regressors for each stimulation condition (before/after stimulation): 1) an indicator function denoting a rating trial; and 2) an indicator function denoting a rating trial multiplied (that is, modulated) by the participants' rating value (0-7 scale) for the face presented in the trial. Both regressors were modeled as stick functions at the onset of stimulus presentation. The model also included motion parameters, session constants and missed trials as regressors of no interest. The regressors of interest and missed trial regressor were convolved with a canonical form of the hemodynamic response. This general linear model also made use of a parametric regressor. These types of regressors look for areas in which the BOLD response varies with the magnitude of a variable of interest (in this case the attractiveness rating). The estimated coefficient for such regressors can be roughly interpreted as a measure of the strength of association between the BOLD response and the variable of interest. Single participant contrasts were calculated for the rating parametric regressor separately for the before- and after-stimulation conditions. These contrasts were motivated by previous work and identified regions where BOLD activity is correlated with attractiveness ratings. Single participant contrasts were calculated for the difference between the parametric regressor for the after-stimulation and before stimulation conditions. This contrast identifies regions where BOLD activity is more correlated with attractiveness ratings after stimulation than before.

Figure 4A:
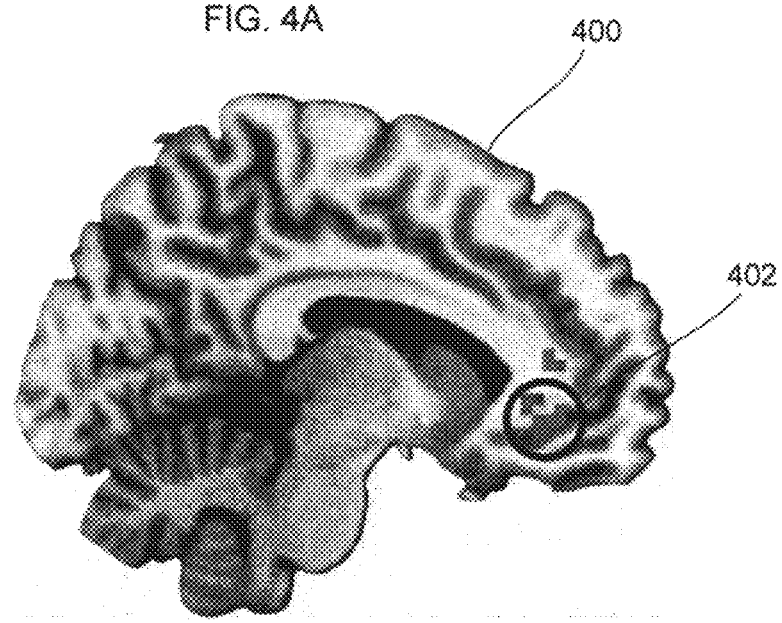
FIG. 4A is an fMRI scan of a common region of the ventromedial prefrontal cortex used in testing.
Figure 4B:
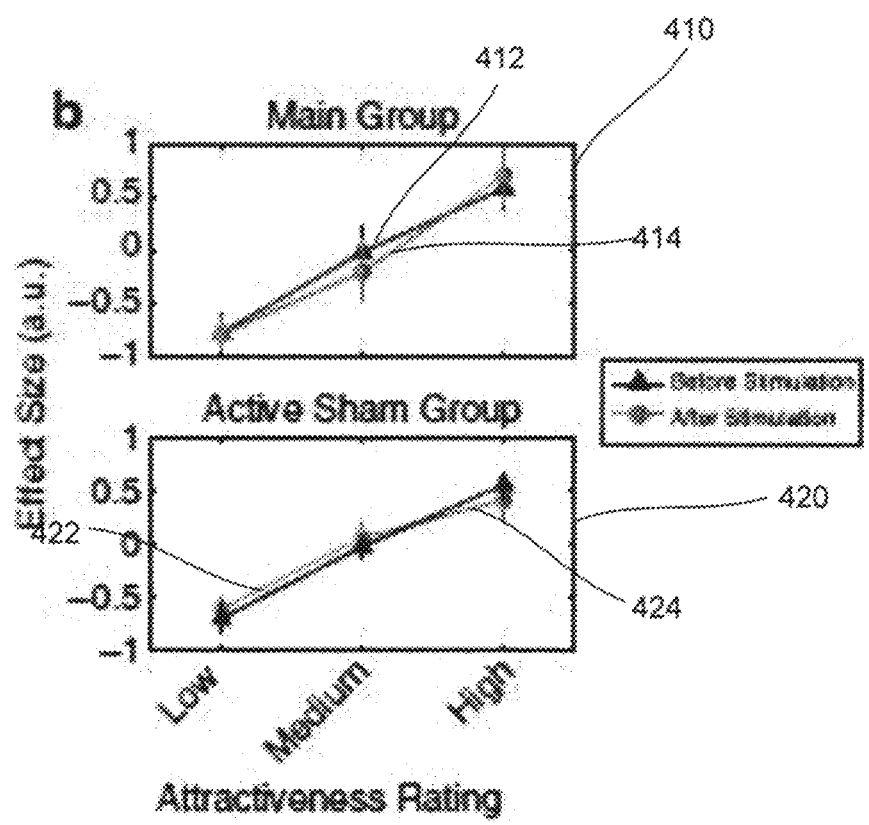
FIG. 4B are graphs of data relating to the increase in effect size of the ventromedial prefrontal cortex in attractiveness testing in the main group.

FIG. 4A-4D are functional magnetic resonance imaging scans and graphs of data based on the results from the attractiveness testing. FIG. 4E is a table of conjunction analysis between regions showing a signal positively correlated with attractiveness ratings before and after stimulation in the main stimulation and the active sham groups in FIG. 3A. FIG. 4F is a table of brain regions showing an interaction between attractiveness ratings before and after stimulation in the main group as compared to the active sham group in FIG. 3A. The tables in FIGS. 4E and 4F include data for all the areas of the brain that were active in the fMRI contrast scans shown in FIGS. 4A and 4C. FIG. 4A is a fMRI scan 400 showing a common region 402 of the ventromedial prefrontal cortex in which activity correlated with attractiveness ratings before and after stimulation, in both the main group and the active sham group shown in FIG. 2A. FIG. 4B shows a graph 410 of the data from the main group before stimulation as shown by line 412 and after stimulation as shown by line 414. FIG. 4B also shows a graph 420 of the data from the active sham group before stimulation as shown by line 422 and after stimulation as shown by line 424. The graphs 410 and 412 show that the effect size in the ventromedial prefrontal cortex 402 increased with attractiveness ratings (lower—lower tertile; medium—middle tertile; high—upper tertile). The imaging data was separated into tertiles to illustrate how brain activity changes with low, medium, and high attractiveness ratings.

Figure 4C:
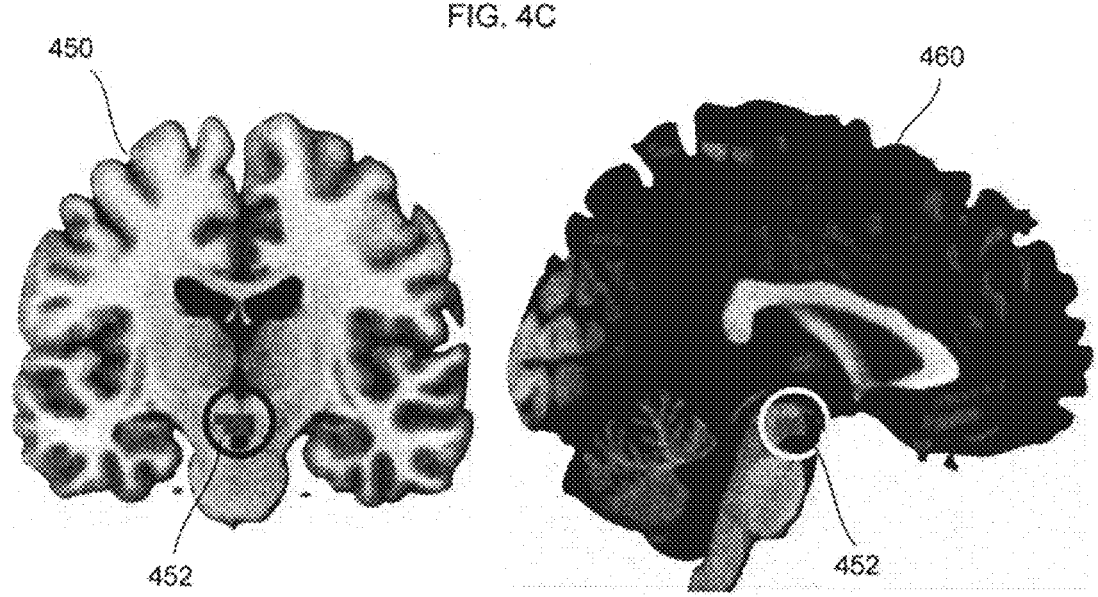
FIG. 4C show fMRI scans of the ventral midbrain activity during testing.
Figure 4D:
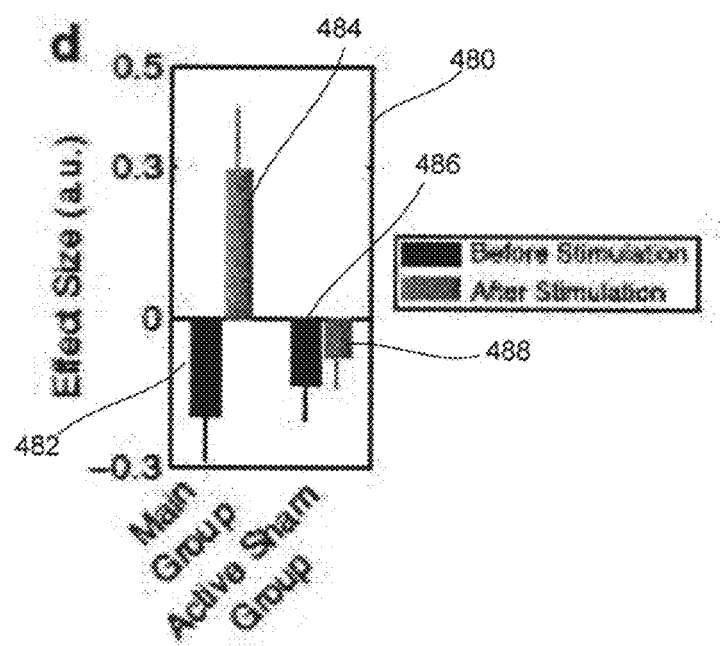
FIG. 4D is a graph of average effect sizes of the main group in contrast with the sham group in the testing.

FIG. 4C shows a top level fMRI scan 450 and a cross section fMRI scan 460 that show a significant increase in activity in the ventral midbrain area 452 from stimulation of the ventromedial prefrontal cortex and the right dorsolateral prefrontal cortex. As will be explained below, an interaction contrast between attractiveness ratings and stimulation revealed a significant increase in ventral midbrain activity from the fMRI scans of the main group as compared with the active sham group. FIG. 4D shows the resulting attractiveness data in a graph 480. A bar 482 shows the average effect size of the main group before stimulation and a bar 484 shows the average effect size of the main group after stimulation. A bar 486 shows the average effect size of the sham group before stimulation and a bar 488 shows the average effect size of the sham group after stimulation. The graph 480 shows average effect sizes representing the correlation between ventral midbrain activity and rating values before and after stimulation in the main and active sham groups. The graph 480 shows that ventral midbrain activity was positively correlated with attractiveness ratings after administration of transcranial direct current stimulation. All contrasts are displayed at $P<0.005$ uncorrected, and significant at $P<0.05$ with small volume corrected arbitrary units (a.u.).

The contrast images computed for each participant were taken to the group random effects level, and conjunctions and comparisons were conducted between the main stimulation group and the active sham group to determine areas showing transcranial direct current stimulation induced changes in activity. A conjunction contrast was computed to identify brain areas with overlapping correlations with attractiveness ratings before and after stimulation in both the main and the active sham groups as shown in the fMRI scan 400 in FIG. 4A. An interaction contrast was also computed between attractiveness ratings and before/after stimulation based on the fMRI scans 450 and 452 in FIG. 4C. For this interaction, differences in activity were examined between the main and active sham groups. For visualization purposes only, all of the images shown are thresholded at $P<0.005$. For inference purposes, the tables in FIGS. 4E and 4F report those areas within a priori regions of interest that survive false discovery rate correction. Region of interest definitions are described below.

The goal of the data analysis was to investigate whether anodal transcranial direct current stimulation of the ventromedial prefrontal cortex, and simultaneous cathodal transcranial direct current stimulation of the right dorsolateral prefrontal cortex in the main stimulation group, caused an increase in the correlation between ventromedial prefrontal cortex activity and activity in the ventral midbrain compared with the active sham group. The analysis proceeded in three steps: First, individual average time series were computed within a 6-mm sphere surrounding individual participant peaks (in both the main and active sham groups) within the functional mask of ventromedial prefrontal cortex 402 shown in the fMRI scan 400 in FIG. 4A. Variance associated with the six motion regressors was removed from the extracted time series. The location of the peak voxels was based on the general linear model described above. The seed time courses were deconvolved, based on the formula for the canonical hemodynamic response, in order to construct a time series of neural activity in the ventromedial prefrontal cortex. This was done following the procedures described in Gitelman D, Penny W, Ashburner J. Friston K. "Modeling Regional And Psychophysiologic Interactions in fMRI: The Importance Of Hemodynamic Deconvolution," *Neuroimage* 2003; 19: 200-207, hereby incorporated by reference.

Second, a general linear model was estimated with the following regressors: 1) an interaction between the neural activity in the seed region and an indicator function for before-stimulation and after-stimulation trials; 2) an indicator function for before-stimulation and after-stimulation trials; and 3) the original BOLD eigenvariate (the average time series from the 6-mm sphere). The first two regressors were convolved with a canonical form of the hemodynamic response function, and the model also included motion parameters as regressors of no interest. The first regressor in this psychophysiological interaction (PPI) identifies areas that exhibit stimulation-related functional connectivity with ventromedial prefrontal cortex. In particular, it identifies areas in which the correlation in BOLD activity with ventromedial prefrontal cortex increases after transcranial direct current stimulation. It is important to note that this PPI analysis did not include participants' behavioral ratings and thus revealed neural responses irrespective of the behavioral results.

Third, single participant contrasts for the first regressor were calculated, and a second-level analysis was performed by calculating the main and active sham groups' contrast coefficients. Post-hoc between-participant regressions. To explore the results further, post-hoc linear regressions were performed for the main and active sham groups. A behavioral measure of the influence transcranial direct current stimulation had on attractiveness ratings was regressed with a neural measure of the impact transcranial direct current stimulation had on connectivity between ventromedial prefrontal cortex and ventral midbrain, separately for the main and active sham groups. The behavioral measure was calculated by subtracting average ratings before stimulation from those after stimulation. The neural measure was the average parameter estimate extracted from the anatomical region of interest 370 in FIG. 3A in the ventral midbrain from the PPI, separately for each stimulation group (main and active sham).

Figure 3B:
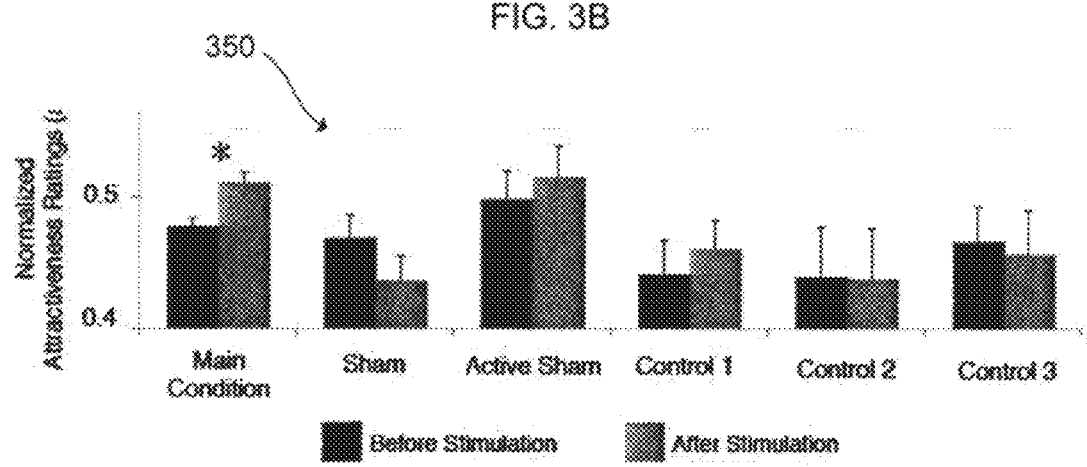
FIG. 3B are graphs of corresponding result data from testing the method of non-invasive treatment.

All results reported in the main text are with a corrected significance threshold of $P<0.05$ based on a small-volume false discovery rate correction within the predefined ROIs. Evaluating the precise location of midbrain fMRI signals is difficult given the small size of the dopaminergic nuclei and problems with group registration in this region. Therefore, the region of interest 370 was defined for the ventral midbrain (encompassing both the substantia nigra and the ventral tegmental area as shown in FIG. 3B. The region of interest of the ventromedial prefrontal cortex was defined as a 10-mm sphere centered at ($x=-3$; $y=38$; $z=-18$). These coordinates were taken from a previous study examining facial attractiveness encoding. All effect sizes within these regions of interest were extracted using the average of all voxels within the region of interest.

As explained above, the participants were stimulated with transcranial direct current stimulation and made attractiveness ratings of a series of faces while being scanned with a functional magnetic resonance imager before and after stimulation. This procedure allowed examination of the neural and behavioral influence of the transcranial direct current stimulation on appraisal of facial attractiveness. This task was selected because it is known to recruit components of neural reward circuits. Rating facial attractiveness is one of the most basic reward appraisal tasks and employs limited cortical regions of the prefrontal cortex (the orbitofrontal cortex and ventromedial prefrontal cortex), which allows for a more straight forward interpretation of the behavioral and neural results and fewer confounds of electrode placement. Behaviorally, following anodal stimulation of ventromedial prefrontal cortex and simultaneous cathodal stimulation of the right dorsolateral prefrontal cortex, participants in the main stimulation group found the presented faces significantly more attractive ($t(18)=2.26$; $P=0.03$) as shown in the graph 350 in FIG. 3B. A number of control conditions were tested in which the location and polarity of transcranial direct current stimulation electrodes were varied as shown in FIG. 3A. None of these control conditions yielded a significant increase in attractiveness ratings following stimulation as shown in the graph 350 in FIG. 3B. Taken together, these control conditions show that the specific combination of electrode placement and anodal/cathodal stimulation in the main stimulation group was critical to cause the behavioral and neural effects reported ($F(2, 52)=5.48$; $P=0.007$).

Testing confirmed that activity in the ventromedial prefrontal cortex 210 is correlated with participants' attractiveness ratings both before and after stimulation. A general linear model of BOLD activity was estimated that included a parametric regressor for attractiveness ratings at the time of evaluation. Activity in the ventromedial prefrontal cortex was correlated with attractiveness ratings for all participants both before and after stimulation as shown in the scans in FIGS. 4A and 4B and the table in FIG. 4E. The area of the ventromedial prefrontal cortex identified overlaps with regions that have been associated with attractiveness ratings in other studies.

Testing confirmed an interaction between attractiveness ratings before and after stimulation revealed an increase in neural activity for attractive faces in ventral midbrain following stimulation in the main group as compared with the active sham group. This reflects a remote stimulation of ventral midbrain in the main stimulation group. The testing used the same general linear model described above. Significant interactions between attractiveness ratings before and after transcranial direct current stimulation in the main group as compared with the active sham group in the region of interest 270 shown in FIG. 2C were found, including the ventral midbrain shown in the scan in FIG. 4C and described in the table in FIG. 4F. This interaction was such that following stimulation in the main group, activity in the ventral midbrain was more positively correlated with attractiveness ratings as shown in the data in the graph 480 in FIG. 4D. The ventral midbrain has been implicated in responses to rewarding stimuli and this interaction suggests that transcranial direct current stimulation in the main group increases responsiveness in this region as compared with the active sham group.

Figure 5A:
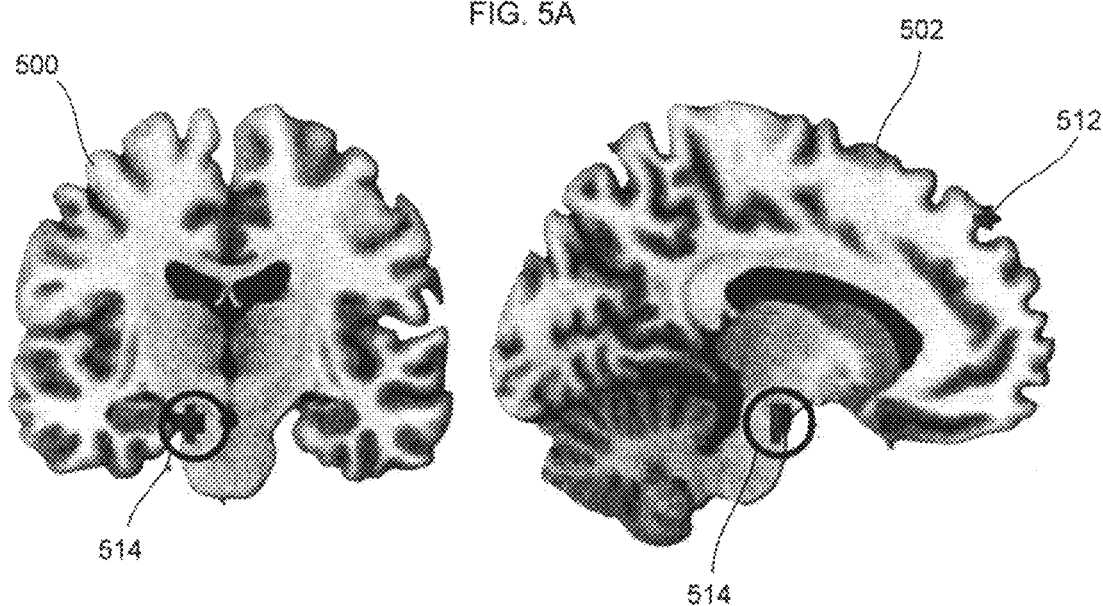
FIG. 5A are fMRI scans showing positive stimulation related functional connectivity of the ventromedial prefrontal cortex to the midbrain.
Figure 5B:
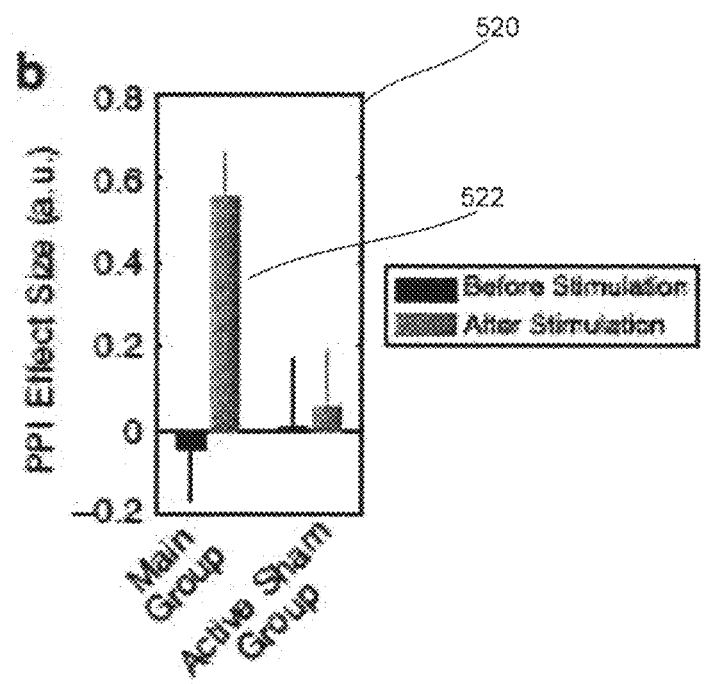
FIG. 5B is a graph of data showing the average effect sizes of the main group and active sham group before stimulation and after stimulation.
Figure 5C:
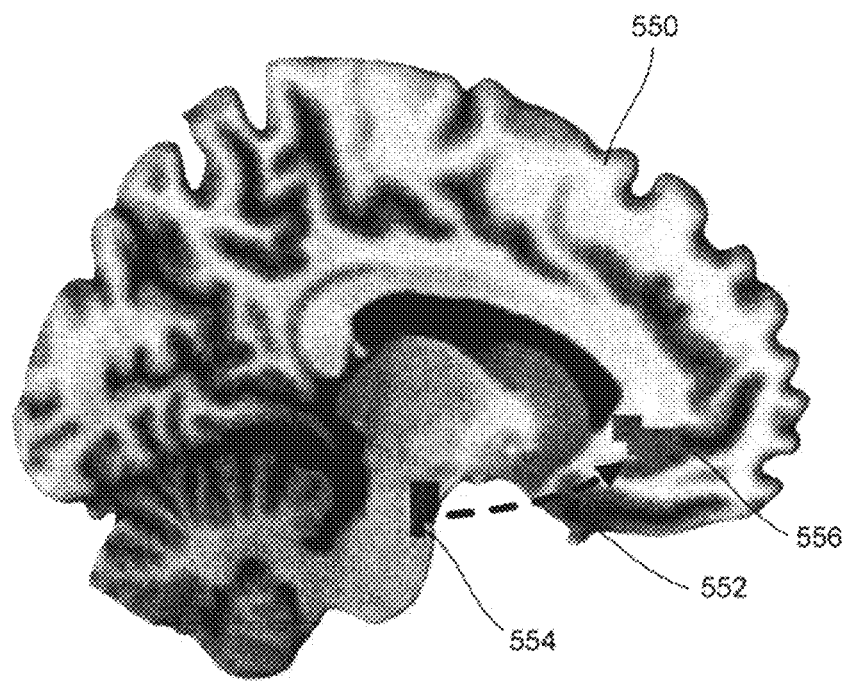
FIG. 5C is an fMRI scan illustrating a path through which stimulation of the ventromedial prefrontal cortex may enhance activity in the ventral midbrain.
Figure 5D:
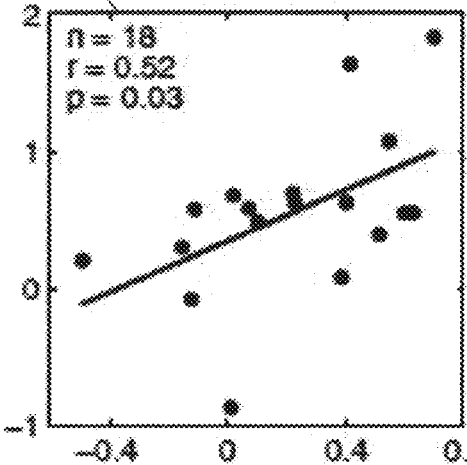
FIG. 5D is a graph of showing data points from the main group for psychophysiological interaction (PPI) effect size and difference in attractiveness rating.
Figure 5D:
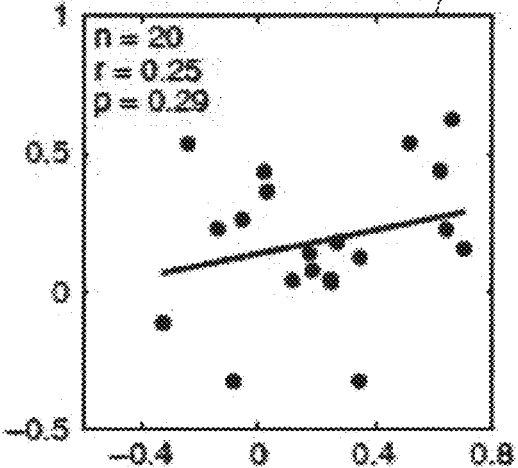

FIG. 5A-5D are functional magnetic resonance imaging scans and graphs of data based on the results of functional connectivity testing. FIG. 5E is a table including regions showing increased stimulation related functional connectivity with the ventromedial prefrontal cortex in the main stimulation group compared to the active sham group. FIG. 5A shows a top level fMRI scan 500 and a cross section fMRI scan 510 that show positive stimulation related functional connectivity of the ventromedial prefrontal cortex 512 with a region 514 of ventral midbrain. FIG. 5B is a graph 520 showing the average effect sizes of the main group and active sham group before stimulation and after stimulation. For the psychophysiological interaction (PPI) contrast, average effect sizes are shown in a bar 522 representing the functional connectivity between seed activity in the ventromedial prefrontal cortex and the ventral midbrain. FIG. 5C is an fMRI scan 550 summarizing the results of the PPI analyses and illustrating a path 552 through which stimulation of the ventromedial prefrontal cortex 554 might enhance activity in the ventral midbrain 556. In the fMRI scan 550, all contrasts are displayed at P<0.005 uncorrected, and significant at P<0.05, small volume corrected arbitrary units (a.u.). FIG. 5D shows a graph 560 showing data points from the main group for PPI effect size and difference in attractiveness rating. Another graph 570 shows data points from the sham group for PPI effect size and difference in attractiveness rating. In the main group, the more enhanced a participants' functional connectivity between these regions following stimulation, the larger their increase in attractiveness ratings following stimulation. One participant in the main group was removed from this analysis because her PPI parameter estimate constituted a statistical outlier (outside two standard deviations of the mean).

It has been confirmed that the ventromedial prefrontal cortex 210 and the ventral midbrain 204 in FIG. 2A exhibit increased functional connectivity following stimulation in the main group compared with the active sham group. A new general linear model was created in which a PPI between before/after stimulation (psychological/task variable) and seed activity in the ventromedial prefrontal cortex (physiological variable) was tested. This model allowed examination of the network effects of ventromedial prefrontal cortex stimulation on other brain regions, with specific interest in the same region of interest used above that encompassed ventral midbrain dopaminergic areas as described in the table in FIG. 4F. A region of the same ventral midbrain region of interest is more correlated with ventromedial prefrontal cortex activity following stimulation in the main stimulation group as compared with the active sham group as shown in the data in the graph 520 in FIG. 5B and described in the table in FIG. 5E. This result suggests that the functional connectivity between ventromedial prefrontal cortex 210 and ventral midbrain 204 is enhanced by transcranial direct current stimulation in the main stimulation group.

It was confirmed that those participants with enhanced connectivity between ventromedial prefrontal cortex and ventral midbrain following stimulation in the main group displayed larger increases in attractiveness ratings. This was tested by performing a linear regression of activities in ventral midbrain identified in the PPI and the differences in participants' mean attractiveness ratings following transcranial direct current stimulation. There was a significant correlation in the main stimulation group (r=0.52, P=0.03) and not the active sham group (r=0.25, P=0.29). This correlation illustrates that those participants with more enhanced connectivity following transcranial direct current stimulation (in the main stimulation group) exhibited the greatest increase in attractiveness ratings as shown by the data charted in the graphs 560 and 570 in FIG. 5D. Thus, anodal stimulation of ventromedial prefrontal cortex increased the functional connectivity between ventromedial prefrontal cortex and ventral midbrain as shown in the fMRI scan 550 in FIG. 5C, and the transcranial direct current stimulation enhancement of these connections caused participants' increases in behavioral ratings.

These results demonstrate that anodal transcranial direct current stimulation of ventromedial prefrontal cortex and cathodal stimulation of the right dorsolateral prefrontal cortex may be used to induce remote changes in regions deep within the brain, which were conventionally thought to be unreachable with noninvasive stimulation techniques. Specifically, remote functional changes may be elicited within the ventral midbrain 204, an area populated with neurons of the substantia nigra 230 and the ventral tegmental area 232 and their efferent projections. Moreover, the attractiveness rating results indicate that these transcranial direct current stimulation induced neural changes have a direct influence on participants' rewarding appraisals. The testing provides simultaneous neural and behavioral evidence consistent with known functions of the remotely stimulated ventral midbrain. Moreover, the neural patterns of functional connectivity induced with a very specific transcranial direct current stimulation electrode configuration (and no other control stimulation conditions) are in concert with the network of projections known to exist between the frontal cortex and ventral midbrain.

The prefrontal cortex has projections that directly interface with the ventral midbrain, while a far larger number of prefrontal connections indirectly couple the frontal cortex and ventral midbrain via the striatum. Significantly increased stimulation-induced connectivity between the prefrontal cortex and the ventral midbrain were found.

Each of these embodiments and obvious variations thereof is contemplated as falling within the spirit and scope of the claimed invention, which is set forth in the following claims.

What is claimed is:

1. A method of stimulating a midbrain interconnected with a prefrontal cortex of a brain, comprising:
    attaching an electrical stimulator near the prefrontal cortex of the brain; and
    stimulating the prefrontal cortex via the electrical stimulator to remotely activate the midbrain of the brain, wherein the prefrontal cortex includes a ventromedial prefrontal cortex and a right dorsolateral prefrontal cortex, and wherein the electrical stimulator includes an anode electrode and a cathode electrode, and wherein stimulating the prefrontal cortex with the electrical stimulator includes coupling the anode electrode to the ventromedial prefrontal cortex and coupling the cathode electrode to the right dorsolateral prefrontal cortex.

2. The method of claim 1, further comprising monitoring activity in the midbrain during the stimulating.

3. The method of claim 2, wherein the monitoring is performed with a functional magnetic resonance imager.

4. The method of claim 2, wherein the monitoring is performed with an electroencephalogram device.

5. The method of claim 2, wherein the stimulating is adjusted based on the activity monitored in the midbrain.

6. The method of claim 1, wherein the electrical stimulator provides a constant stimulus to prefrontal cortex.

7. The method of claim 1, wherein the stimulator is a transcranial direct current stimulator (tDCS).

8. The method of claim 1, wherein a contact area of the anode electrode is smaller than a contact area of the cathode electrode.

9. The method of claim 1, wherein the midbrain is connected directly to the prefrontal cortex.

10. The method of claim 1, wherein a striatum of the brain is indirectly coupled to the prefrontal cortex and stimulated remotely.

* * * * *